United States Patent
Scott et al.

(10) Patent No.: US 7,338,652 B2
(45) Date of Patent: *Mar. 4, 2008

(54) METHODS FOR POSITRON EMISSION IMAGING WITH RADIOLABELED HALOGENATED XANTHENES DIAGNOSTIC AGENTS

(75) Inventors: Timothy C. Scott, Knoxville, TN (US); H. Craig Dees, Knoxville, TN (US); Eric A. Wachter, Oak Ridge, TN (US)

(73) Assignee: Provectus Pharmatech, Inc., Knoxville, TN (US)

( * ) Notice: Subject to any disclaimer, the term of this patent is extended or adjusted under 35 U.S.C. 154(b) by 234 days.

This patent is subject to a terminal disclaimer.

(21) Appl. No.: 11/050,512

(22) Filed: Feb. 3, 2005

(65) Prior Publication Data

US 2005/0276753 A1    Dec. 15, 2005

Related U.S. Application Data

(60) Provisional application No. 60/578,622, filed on Jun. 10, 2004.

(51) Int. Cl.
*A61K 49/04*    (2006.01)

(52) U.S. Cl. ................... 424/9.45; 424/1.81; 424/1.85; 424/1.65; 424/9.1; 424/9.4; 424/1.89; 424/9.44; 424/9.451

(58) Field of Classification Search ............... 424/1.11, 424/1.65, 1.81, 1.85, 1.89, 9.1, 9.4, 9.45, 424/9.451, 9.44; 600/411, 420, 427, 431; 549/200

See application file for complete search history.

(56) References Cited

U.S. PATENT DOCUMENTS 6,493,570 B1 * 12/2002 Dees et al. ................. 600/411

FOREIGN PATENT DOCUMENTS

GB        846674        8/1960

OTHER PUBLICATIONS

PCT International Search Report and Written Opinion for PCT/US05/16836 dated Nov. 17, 2005.

* cited by examiner

*Primary Examiner*—Dameron L. Jones
(74) *Attorney, Agent, or Firm*—Cook, Alex, McFarron, Manzo, Cummings & Mehler, Ltd.

(57) ABSTRACT

New diagnostic agents for positron emission tomography (PET) and methods for use of such agents for imaging of human or animal tissue are described, wherein a primary active component of such agents is a radiolabeled halogenated xanthene or halogenated xanthene derivative. Preferably, the radiolabeled halogenated xanthene is radiolabeled Rose Bengal or a functional derivative of Rose Bengal.

4 Claims, 1 Drawing Sheet

METHODS FOR POSITRON EMISSION IMAGING WITH RADIOLABELED HALOGENATED XANTHENES DIAGNOSTIC AGENTS

This application claims the benefit of U.S. provisional application No. 60/578,622 filed Jun. 10, 2004.

BACKGROUND OF THE INVENTION

The present invention is directed to new diagnostic agents, and methods of use of such agents, for medical imaging using positron emission tomography (PET). PET is a nuclear medicine imaging technique which produces a three dimensional image of the body. PET imaging is commonly used to obtain non-invasive information about internal body structures and tissues and the function and health of such structures and tissues. PET uses a metabolically active molecule and a short-lived radioactive tracer isotope (to radiolabel the active molecule) as a diagnostic agent. The isotope decays by emitting a positron. When a PET diagnostic agent is administered to the body, it is retained or accumulates in certain tissues of interest, thereby facilitating imaging of those tissues based upon detection of gamma ray photons produced upon annihilation of positrons emitted from the radiolabeled PET diagnostic agent. Such annihilation occurs when an emitted positron collides with an electron present in the vicinity of emission, resulting in production of two 511 keV photons that are emitted in nearly opposite directions. Typically, such PET diagnostic agents are radiolabeled with (i.e., contain) one or more atoms that exhibit positron emission (such as certain isotopes of carbon, nitrogen, oxygen, fluorine, or rubidium, including $^{11}C$, $^{13}N$, $^{15}O$, $^{18}F$, and $^{82}Rb$). The effects of the emitted positrons (i.e., the subsequently emitted gamma ray photons) are detected by a detection device located outside the body which typically converts raw data into two- or three-dimensional images of the region of interest. The results are then read by a nuclear medicine physician or radiologist to interpret the results in terms of the patient's diagnosis and treatment.

Considerable effort has been invested in development of PET diagnostic agents in an effort to improve contrast between various anatomical features, such as between cancerous and non-cancerous tissues. Continued progress in medical science mandates improved options in such diagnostic capability, which in turn mandates further development of improved diagnostic agents.

Therefore, it is one object of the present invention to meet these characteristics, to overcome the drawbacks in prior methods and agents and to provide an improvement over these prior methods and agents.

SUMMARY OF THE INVENTION

The present invention is directed to certain diagnostic agents for PET imaging and methods for using such agents exhibiting positron emission.

In a preferred embodiment, a primary component of such diagnostic agent is a halogenated xanthene or a functional derivative of a halogenated xanthene that has been radiolabeled with one or more positron emitting isotopes of carbon, oxygen, fluorine, chlorine, bromine, or iodine, including $^{10}C$, $^{11}C$, $^{13}O$, $^{14}O$, $^{15}O$, $^{17}F$, $^{18}F$, $^{32}Cl$, $^{33}Cl$, $^{34}Cl$, $^{74}Br$, $^{75}Br$, $^{76}Br$, $^{77}Br$, $^{78}Br$, $^{117}I$, $^{118}I$, $^{119}I$, $^{120}I$, $^{121}I$, $^{122}I$, $^{124}I$, $^{126}I$, and $^{128}I$. In a further preferred embodiment, this radiolabeled halogenated xanthene is Rose Bengal or a functional derivative of Rose Bengal.

The present invention is also directed to a method for imaging human or animal tissue comprising the steps of:
 administering a diagnostic agent to a patient, a portion of said diagnostic agent being retained in tissue of interest, said diagnostic agent emitting positrons; and
 imaging said tissue based on the effects of said positrons emitted from the diagnostic agent,
 wherein said diagnostic agent is a radiolabeled halogenated xanthene.

DETAILED DESCRIPTION OF THE PRESENTLY PREFERRED EMBODIMENT

The present invention is directed to certain diagnostic agents for PET imaging and methods for using such agents exhibiting positron emission. In a preferred embodiment, a primary component of such diagnostic agent is a halogenated xanthene or a functional derivative of a halogenated xanthene that has been radiolabeled with one or more positron emitting isotopes of carbon, oxygen, fluorine, chlorine, bromine, or iodine, including $^{10}C$, $^{11}C$, $^{13}O$, $^{14}O$, $^{15}O$, $^{17}F$, $^{18}F$, $^{32}Cl$, $^{33}Cl$, $^{34}Cl$, $^{74}Br$, $^{75}Br$, $^{76}Br$, $^{77}Br$, $^{78}Br$, $^{117}I$, $^{118}I$, $^{119}I$, $^{120}I$, $^{121}I$, $^{122}I$, $^{124}I$, $^{126}I$, and $^{128}I$. In a further preferred embodiment, this radiolabeled halogenated xanthene is Rose Bengal (i.e., 4,5,6,7-tetrachloro-2',4',5',7'-tetraiodofluorescein) or a functional derivative of Rose Bengal.

The halogenated xanthenes constitute a family of extremely useful agents that can be selectively and safely delivered at high concentrations to certain tissues. Certain properties of the halogenated xanthenes are described in U.S. Ser. No. 09/184,388, filed on Nov. 2, 1998, in U.S. Ser. No. 09/216,787, filed on Dec. 21, 1998, in U.S. Ser. No. 09/635,276, filed on Aug. 9, 2000, in U.S. Ser. No. 09/799,785, filed on Mar. 6, 2001, in U.S. Ser. No. 09/817,448, filed on Mar. 26, 2001, in U.S. Ser. No. 09/900,355, filed on Jul. 6, 2001, and in U.S. Ser. No. 10/314,840, filed on Dec. 9, 2002, which are herein incorporated by reference in their entirety. In general, the halogenated xanthenes are characterized by a low cytotoxicity (toxicity to cells) at low concentration, a propensity for selective concentration or retention in certain tissues and cells, a high cytotoxicity upon such concentration or retention, and by chemical and physical properties that are substantially unaffected by the local chemical environment or by the attachment of functional derivatives at positions $R^1$ and $R^2$ described below.

Figure 1A:
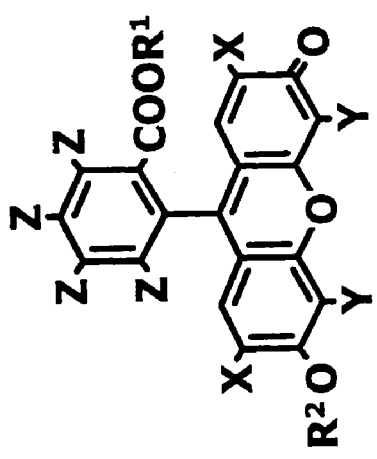
FIG. 1a is an illustration of the chemical structure of a halogenated xanthene.
Figure 1B:
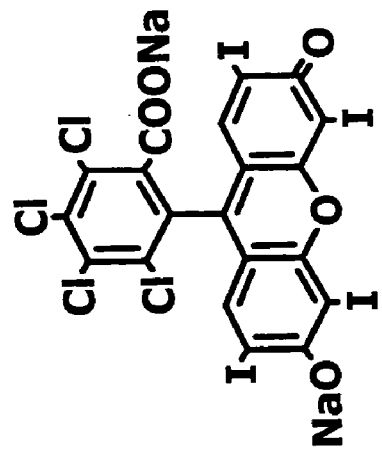
FIG. 1b is an illustration of the chemical structure of Rose Bengal.

The generalized chemical structure of the halogenated xanthenes is illustrated in FIG. 1a, where the symbols X, Y. and Z represent various elements present at the designated positions, and the symbols $R^1$ and $R^2$ represent various functionalities present at the designated positions. The chemical structure of a specific example of a halogenated xanthene, Rose Bengal, is illustrated in FIG. 1b. Physical properties of representative halogenated xanthenes are summarized in attached Table 1. In general, the halogenated xanthenes have the empirical formula, $C_{20}H_nO_5F_aCl_bBr_cI_d$, $R^1,R^2$, where $n \geq 2$, and a, b, c, and d are integers greater than or equal to zero. For example, the empirical formula for the disodium salt of Rose Bengal is $C_{20}H_2O_5F_0Cl_4Br_0I_4,R^1,R^2$, where $R^1$ and $R^2$ each represent a sodium atom, or, more simply, $C_{20}H_2O_5Cl_4I_4,Na_2$.

In their non-radiolabeled form, the halogenated xanthenes are useful as food dyes, biological stains, photosensitizers (i.e. agents which are used with light for photodynamic imaging or treatment as for example disclosed in U.S. Ser. Nos. 09/635,276 and 09/799,785), radiosensitizers (i.e., agents that are used with applied ionizing radiation for imaging and radiation treatment as for example disclosed in U.S. Ser. Nos. 09/216,787 and 09/817,448), and as chemoablative or chemotherapeutic agents (as for example disclosed in U.S. Ser. No. 09/900,355). When labeled with certain gamma-emitting isotopes of iodine (i.e., $^{113}$I and $^{125}$I), one of the halogenated xanthenes (Rose Bengal) has proven useful for diagnosis of hepatic function based on either measurement of differential excretion or imaging of the pattern of gamma emission from such radiolabeled molecules (for example as disclose in Serafini et al., J. Nucl. Med. 16 (1975) 629-633).

The present inventors were part of a team that has previously discovered and disclosed that the halogenated xanthenes exhibit selective retention in certain types of tissue, especially those exhibiting cancerous or precancerous conditions (i.e., neoplasia, dysplasia, and hyperplasia), as disclosed in U.S. Ser. Nos. 09/635,276, 09/799,785, 09/216, 787, 09/817,448, and 09/900,355. Such retention can be useful for diagnosis (for example, using x-ray computed tomography or ultrasound imaging) and for therapy (for example, using photodynamic therapy or radiosensitization).

The present inventors have now discovered new isotopically-labeled (i.e., radiolabeled) members of the halogenated xanthene family that are capable of serving as diagnostic agents for PET imaging. More specifically, Applicants have created new halogenated xanthene compounds wherein a halogenated xanthene or a functional derivative of a halogenated xanthene has been radiolabeled with one or more positron emitting isotope of carbon, oxygen, fluorine, chlorine, bromine, or iodine, including $^{10}$C, $^{11}$C, $^{13}$O, $^{14}$O, $^{15}$O, $^{17}$F, $^{18}$F, $^{32}$Cl, $^{33}$Cl,$^{34}$Cl, $^{74}$Br, $^{75}$Br, $^{76}$Br, $^{77}$Br, $^{78}$Br, $^{117}$I, $^{118}$I, $^{119}$I, $^{120}$I, $^{121}$I, $^{122}$I, $^{124}$I, $^{126}$I, and $^{128}$I. One skilled in the art can synthesize and produce these new compounds using known chemistry of the halogenated xanthenes with the additional information provided in this application. For example, the synthesis and production of non-radiolabeled halogenated xanthenes and the chemistry of such compounds is known. Labeling with radioisotopes, such as for example the preferred radioisotopes of bromine or iodine (i.e., $^{74}$Br, $^{75}$Br, $^{76}$Br, $^{77}$Br, $^{78}$Br, $^{117}$I, $^{118}$I, $^{119}$I, $^{120}$I, $^{121}$I, $^{122}$I, $^{124}$I, $^{126}$I, and $^{128}$I), can be achieved by using standard halogen exchange methods, such as those taught in Serafini, supra. For these radioisotopes and the other radioisotopes listed herein, radiolabeling can be achieved using radiolabeled starting materials in the synthesis of the desired halogenated xanthene (such as for example radiolabeled resorcinol or a radiolabeled phthalic anhydride), thereby directly synthesizing the radiolabeled xanthene.

The present inventors have further discovered that a halogenated xanthene or a functional derivative of a halogenated xanthene that has been radiolabeled with one or more positron emitting isotope of carbon, oxygen, fluorine, chlorine, bromine, or iodine, including $^{10}$C, $^{11}$C, $^{13}$O, $^{14}$O, $^{15}$O, $^{17}$F, $^{18}$F, $^{32}$Cl, $^{33}$Cl, $^{34}$Cl, $^{74}$Br, $^{75}$Br, $^{76}$Br, $^{77}$Br, $^{78}$Br, $^{117}$I, $^{118}$I, $^{119}$I, $^{120}$I, $^{121}$I, $^{122}$I, $^{124}$I, $^{126}$I, and $^{128}$I, can be useful as the active substance in a diagnostic agent for PET imaging. This non-naturally-occurring, novel composition of matter will retain the desirable specificity, toxicity, and other salient pharmaceutical properties of the halogenated xanthenes, as discussed above. Some of the important physical properties of the preferred positron emitting isotopes of carbon, oxygen, fluorine, chlorine, bromine, and iodine are summarized in attached Table 2. Because positron emitting isotopes with very short half-lives may in general be impractical for use in diagnostic procedures due to logistic difficulties in their timely production and subsequent delivery to the patient, those isotopes exhibiting half-lives in excess of approximately one minute are preferred and are more useful. These preferred longer-lived positron emitting isotopes include $^{11}$C, $^{15}$O, $^{18}$F, $^{34}$Cl, $^{74}$Br, $^{75}$Br, $^{76}$Br, $^{77}$Br, $^{78}$Br, $^{117}$I, $^{118}$I, $^{119}$I, $^{120}$I, $^{121}$I, $^{122}$I, $^{124}$I, $^{126}$I, and $^{128}$I. Because the distance traveled by the emitted positron prior to annihilation adversely affects image resolution (where traveled distance is proportional to positron energy), those longer-lived isotopes emitting lower energies are more preferred. Hence, the more preferred longer-lived, lower-energy positron emitting isotopes include $^{11}$C, $^{18}$F, $^{75}$Br, $^{77}$Br, $^{121}$I, $^{124}$I, and $^{126}$I.

Thus, a diagnostic agent containing a halogenated xanthene radiolabeled with one or more of the aforementioned positron emitting elements can be used as a diagnostic agent for PET.

Hence, one preferred embodiment of the present invention is a diagnostic agent that contains, as an active ingredient at a concentration of from greater than approximately 0.001% to less than approximately 20%, at least one halogenated xanthene radiolabeled with one or more positron emitting isotope selected from the group of $^{10}$C, $^{11}$C, $^{13}$O, $^{14}$O, $^{15}$O, $^{17}$F, $^{18}$F, $^{32}$Cl, $^{33}$Cl, $^{34}$Cl, $^{74}$Br, $^{75}$Br, $^{76}$Br, $^{77}$Br, $^{78}$Br, $^{117}$I, $^{118}$I, $^{119}$I, $^{120}$I, $^{121}$I, $^{122}$I, $^{124}$I, $^{126}$I, and $^{128}$I (i.e., a radiolabeled halogenated xanthene). It is further preferred that this radiolabeled halogenated xanthene is radiolabeled with one or more longer-lived positron isotope selected from the group of $^{11}$C, $^{15}$O, $^{18}$F, $^{34}$Cl, $^{74}$Br, $^{75}$Br, $^{76}$Br, $^{78}$Br, $^{117}$I, $^{118}$I, $^{119}$I, $^{120}$I, $^{121}$I, $^{122}$I, $^{124}$I, $^{126}$I, and $^{128}$I. It is further preferred that this radiolabeled halogenated xanthene is radiolabeled with one or more longer-lived, lower-energy positron emitting isotopes selected from the group of $^{11}$C, $^{18}$F, $^{75}$Br, $^{77}$Br, $^{121}$I, $^{124}$I, and $^{126}$I.

It is further preferred that this radiolabeled halogenated xanthene is radiolabeled Rose Bengal.

Examples of radiolabeled halogenated xanthenes which can be used in the diagnostic agent of the present invention include one or more of the following:

radiolabeled 4',5'-Dichlorofluorescein;
radiolabeled 2',7'-Dichlorofluorescein;
radiolabeled 4,5,6,7-Tetrachlorofluorescein;
radiolabeled 2',4',5',7'-Tetrachlorofluorescein;
radiolabeled Dibromofluorescein;
radiolabeled Solvent Red 72;
radiolabeled Diiodofluorescein;
radiolabeled Eosin B;
radiolabeled Eosin Y;
radiolabeled Ethyl Eosin;
radiolabeled Erythrosin B;
radiolabeled Phloxine B;
radiolabeled Rose Bengal;
radiolabeled 4,5,6,7-Tetrabromoerythrosin;
radiolabeled Mono-, Di-, or Tribromoerythrosin;
radiolabeled Mono-, Di-, or Trichloroerythrosin;
radiolabeled Mono-, Di-, or Trifluoroereyhrosin;
radiolabeled 2',7'-Dichloro-4,5,6,7-Tetrafluorofluorescein;
radiolabeled 2',4,5,6,7,7'-Hexafluorofluorescein;
radiolabeled 4,5,6,7-Tetrafluorofluorescein;
radiolabeled 2',4',5,5',6,7'-Hexaiodofluorescein;
radiolabeled 2',4',5,5',7,7'-Hexaiodofluorescein;
radiolabeled 2',4',5',6,7,7'-Hexaiodofluorescein;

radiolabeled 2', 4',5,5',6,7,7'-Heptaiodofluorescein;
radiolabeled 4-Chloro-2',4',5,5',6,7'-hexaiodofluorescein;
radiolabeled 4-Chloro-2',4',5,5',7,7'-hexaiodofluorescein;
radiolabeled 4-Chloro-2',4',5',6,7,7'-hexaiodofluorescein;
radiolabeled 4-Chloro-2',4',5,5',6,7,7'-heptaiodofluorescein;
radiolabeled 4,5-Dichloro-2',4',5',6,7,7'-hexaiodofluorescein;
radiolabeled 4,6-Dichloro-2',4',5,5',7,7'-hexaiodofluorescein; and
radiolabeled 4,7-Dichloro-2',4',5,5',6,7'-hexaiodofluorescein, wherein said radiolabel comprises incorporation of one or more positron emitting isotope selected from the group of $^{10}C$, $^{11}C$, $^{13}O$, $^{14}O$, $^{15}O$, $^{17}F$, $^{18}F$, $^{32}Cl$, $^{33}Cl$, $^{34}Cl$, $^{74}Br$, $^{75}Br$, $^{76}Br$, $^{77}Br$, $^{78}Br$, $^{117}I$, $^{118}I$, $^{119}I$, $^{120}I$, $^{121}I$, $^{122}I$, $^{124}I$, $^{126}I$, and $^{128}I$.

In an alternate preferred embodiment, positron emission tomography is used to image, detect or otherwise observe the presence of a diagnostic agent that contains, at a concentration of from greater than approximately 0.001% to less than approximately 20%, at least one radiolabeled halogenated xanthene. It is further preferred that this diagnostic agent include the radiolabeled form of the halogenated xanthene Rose Bengal.

This description has been offered for illustrative purposes only and is not intended to limit the invention of this application.

TABLE 1

Physical properties of some example halogenated xanthenes (non-radiolabeled).

| Compound | Substitution | | | | | MW (g) |
|---|---|---|---|---|---|---|
| | X | Y | Z | R$^1$ | R$^2$ | |
| 4',5'-Dichlorofluorescein | Cl | H | H | Na | Na | 445 |
| 2',7'-Dichlorofluorescein | H | Cl | H | Na | Na | 445 |
| 4,5,6,7-Tetrachlorofluorescein | H | H | Cl | H | H | 470 |
| 2',4',5',7'-Tetrachlorofluorescein | Cl | Cl | H | Na | Na | 514 |
| Dibromofluorescein | Br | H | H | Na | Na | 534 |
| Solvent Red 72 | H | Br | H | H | H | 490 |
| Diiodofluorescein | I | H | H | Na | Na | 628 |
| Eosin B | NO$_2$ | Br | H | Na | Na | 624 |
| Eosin Y | Br | Br | H | Na | Na | 692 |
| Ethyl Eosin | Br | Br | H | C$_2$H$_5$ | K | 714 |
| Erythrosin B | I | I | H | Na | Na | 880 |
| Phloxine B | Br | Br | Cl | Na | Na | 830 |
| Rose Bengal | I | I | Cl | Na | Na | 1018 |
| 4,5,6,7-Tetrabromoerythrosin | I | I | Br | Na | Na | 1195 |

TABLE 2

Isotopes of relevance for PET with the halogenated xanthenes.

| Element | Isotope | Positron Emission Half-Life | Emission Energy (MeV) |
|---|---|---|---|
| Carbon | $^{10}C$ | 19 sec | 1.9 |
| | $^{11}C$ | 20 min | 1.0 |
| Oxygen | $^{13}O$ | 0.009 sec | 6.4 |
| | $^{14}O$ | 71 sec | 1.8 |
| | $^{15}O$ | 124 sec | 1.7 |
| Fluorine | $^{17}F$ | 66 sec | 1.7 |
| | $^{18}F$ | 110 min | 0.6 |
| Chlorine | $^{32}Cl$ | 0.3 sec | 9.5 |
| | $^{33}Cl$ | 2.5 sec | 4.5 |
| | $^{34}Cl$ | 32 min | 2.5 |
| Bromine | $^{74}Br$ | 36 min | 4.7 |
| | $^{75}Br$ | 1.7 hours | 0.3 |
| | $^{76}Br$ | 16.1 hours | 1.2-3.6 |
| | $^{77}Br$ | 57 hours | 0.4 |
| | $^{78}Br$ | 6.4 min | 1.9 |
| Iodine | $^{117}I$ | 7 min | |
| | $^{118}I$ | 14 min | 5.5 |
| | $^{119}I$ | 19 min | |
| | $^{120}I$ | 1.3 hours | 2.1-4.0 |
| | $^{121}I$ | 2.1 hours | 1.2 |
| | $^{122}I$ | 3.5 min | 1.8-3.1 |
| | $^{124}I$ | 4.2 days | 0.8-2.1 |
| | $^{126}I$ | 13 days | 1.1 |
| | $^{128}I$ | 25 min | |

We claim:

1. A method for imaging human or animal tissue comprising the steps of:
   administering a diagnostic agent to a patient, a portion of said diagnostic agent being retained in tissue of interest, said diagnostic agent emitting positrons; and
   imaging said tissue based on detection of gamma ray photons produced upon annihilation of said positrons emitted from the diagnostic agent,
   wherein said diagnostic agent comprises a positron emitting radiolabeled halogenated xanthene, and
   wherein said radiolabel halogenated xanthene comprises incorporation, into said halogenated xanthene, of one or more positron emitting isotopes selected from the group consisting of $^{10}C$, $^{11}C$, $^{13}O$, $^{14}O$, $^{15}O$, $^{17}F$, $^{18}F$, $^{32}Cl$, $^{33}Cl$, $^{34}Cl$, $^{74}Br$, $^{75}Br$, $^{76}Br$, $^{77}Br$, $^{78}Br$, $^{117}I$, $^{118}I$, $^{119}I$, $^{120}I$, $^{121}I$, $^{122}I$, $^{124}I$, $^{126}I$, and $^{128}I$.

2. The method of claim 1 wherein said radiolabeled halogenated xanthene is present in a concentration of greater than about 0.001% to less than about 20%.

3. The method of claim 1 wherein said radiolabeled halogenated xanthene is radiolabeled Rose Bengal.

4. The method of claim 1 wherein said radiolabeled halogenated xanthene is selected from the group consisting of radiolabeled 4',5'-Dichlorolluorescein, radiolabeled 2',7'-Dichlorofluorescein, radiolabeled 4,5,6,7-Tetrachiorofluorescein, radiolabeled 2',4',5',7'-Tetrachlorofluorescein, radiolabeled Dibromofluorescein, radiolabeled Solvent Red 72, radiolabeled Diiodofluorescein, radiolabeled Eosin B, radiolabeled Eosin Y, radiolabeled Ethyl Eosin, radiolabeled Erythrosin B, radiolabeled Phloxine B, radiolabeled 4,5,6,7-Tetrabromoerythrosin, radiolabeled Mono-, Di-, or Tribromoerythrosin, radiolabeled Mono-, Di-, or Trichloroerythrosin, radiolabeled Mono-, Di-, or Trifluoroerythrosin, radiolabeled 2',7'-Dichloro-4,5,6,7-Tetrafluorofluorescein, radiolabeled 2',4,5,6,7,7'-Hexafluorofluorescein, radiolabeled 4,5,6,7-Tetrafluorofluorescein, radiolabeled 2',4',5,5', 6,7'-Hexaiodofluorescein, radiolabeled 2',4',5,5',7,7'-Hexaiodofluorescein, radiolabeled 2',4',5',6,7,7'-Hexaiodofluorescein, radiolabeled 2',4',5,5',6,7,7'-Heptaiodofluorescein, radiolabeled 4-Chloro-2',4',5,5',6,7'-hexaiodoiluorescein, radiolabeled 4-Chloro-2',4',5,5',7,7'-hexaiodofluorescein, radiolabeled 4-Chloro -2',4',5',6,7,7'-hexaiodofluorescein, radiolabeled 4-Chloro-2',4',5,5',6,7,7'-heptaiodofluorcscein, radiolabeled 4,5-Dichloro-2',4',5',6,7, 7'-hexaiodofluorescein, radiolabeled 4,6-Dichloro-2',4',5,5', 7,7'-hexaiodofluorescein, and radiolabeled 4,7-Dichloro-2', 4',5,5', 6,7'-hexaiodofluorescein.

* * * * *